(12) United States Patent
Brennen et al.

(10) Patent No.: US 6,919,162 B1
(45) Date of Patent: Jul. 19, 2005

(54) METHOD FOR PRODUCING HIGH-STRUCTURE AREA TEXTURING OF A SUBSTRATE, SUBSTRATES PREPARED THEREBY AND MASKS FOR USE THEREIN

(75) Inventors: Reid A. Brennen, San Francisco, CA (US); Sally A. Swedberg, Palo Alto, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

(21) Appl. No.: 09/233,694

(22) Filed: Jan. 19, 1999

Related U.S. Application Data
(60) Provisional application No. 60/098,350, filed on Aug. 28, 1998.

(51) Int. Cl.$^7$ ............................................. B23K 26/00
(52) U.S. Cl. .............................. 430/272.1; 430/275.1; 430/322; 219/121.69; 219/121.66; 219/121.68
(58) Field of Search .................... 430/272.1, 275.1, 430/302, 311, 313, 314, 322, 323; 219/121.66, 121.68, 121.69

(56) References Cited

U.S. PATENT DOCUMENTS

| | | | |
|---|---|---|---|
| 4,032,861 A | * | 6/1977 | Rothrock ................... 372/103 |
| 4,478,677 A | | 10/1984 | Chen et al. |
| 4,490,210 A | | 12/1984 | Chen et al. |
| 4,490,211 A | | 12/1984 | Chen et al. |
| 4,923,772 A | | 5/1990 | Kirch et al. .................. 430/5 |
| 5,005,872 A | | 4/1991 | Lass et al. |
| 5,322,988 A | | 6/1994 | Russell et al. |
| 5,500,071 A | | 3/1996 | Kaltenbach et al. |
| 5,571,410 A | | 11/1996 | Swedberg et al. |
| 5,635,089 A | | 6/1997 | Singh |
| 5,658,413 A | | 8/1997 | Kaltenbach et al. |
| 5,882,827 A | | 3/1999 | Nakao |
| 5,968,595 A | | 10/1999 | Kutscher |
| 6,285,443 B1 | | 9/2001 | Wangler et al. |

FOREIGN PATENT DOCUMENTS

| | | |
|---|---|---|
| JP | 7-80675 | 3/1995 |
| JP | 7-241690 | 9/1995 |

OTHER PUBLICATIONS

Becker et al. (1998), "Planar Quartz Chips with Submicron Channels for Two–Dimensional Capillary Electrophoresis Applications," *J. Micromech. Microeng.* 8:24–28.

He et al. (1998), "Fabrication of Nanocolumns for Liquid Chromatography," *Anal. Chem.* 70(18):3790–3797.

Krajnovich et al., "Formation of 'Intrinsic' Surface Defects During 248 mn Photoablation of Polyimide," *J. Appl Phys.* 73:3001–3008 (1993).

* cited by examiner

*Primary Examiner*—Christopher G. Young

(57) ABSTRACT

A method is provided for preparing high-surface area texturing of a substrate using methods by which material from a substrate is subtracted from or added to the surface of the substrate. In one embodiment, the method is a subtractive lithographic method that involves exposing a laser-ablatable substrate, such as a polymeric or ceramic substrate, to laser light. A mask may be used to define the pattern of light incident on the substrate. High-surface area textured substrates, in particular, miniaturized planar analysis devices having high-surface area textured features, prepared by the methods disclosed herein are also provided. A method by which the high-surface area textured substrate or the miniaturized planar analysis device is used as a master from which replicate copies thereof may be made is also provided.

4 Claims, 12 Drawing Sheets

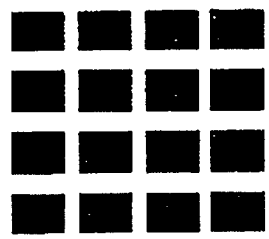
FIG. 2A
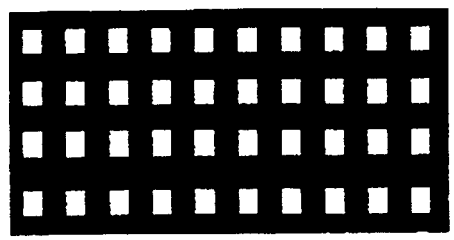
FIG. 2B
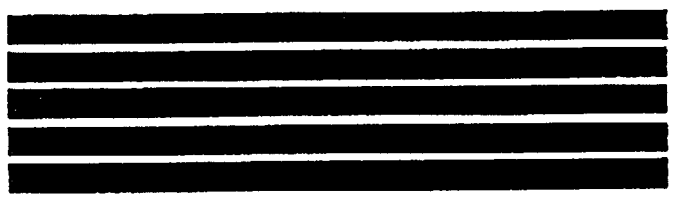
FIG. 3A
FIG. 3B
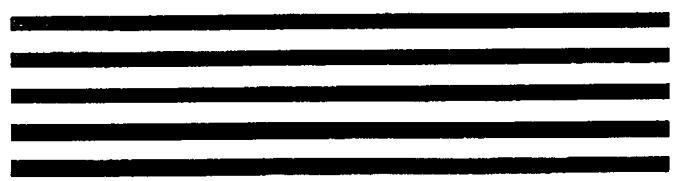

METHOD FOR PRODUCING HIGH-STRUCTURE AREA TEXTURING OF A SUBSTRATE, SUBSTRATES PREPARED THEREBY AND MASKS FOR USE THEREIN

CROSS-REFERENCE TO RELATED APPLICATION

This application is related to provisional patent application Ser. No. 60/098,350, filed Aug. 28, 1998, from which priority is claimed under 35 USC §119(e)(1) and which is incorporated herein by reference in its entirety.

TECHNICAL FIELD

The invention relates generally to methods of preparing analytical devices. In particular, the invention relates to a method of preparing a substrate having high-surface area texturing and substrates prepared by this method. In addition, the present invention relates generally to miniaturized planar analysis devices for liquid phase analysis, and more particularly to fabrication of high-surface area textured microstructures in substrates.

BACKGROUND OF THE INVENTION

Several approaches towards miniaturization for liquid phase analysis have developed in the art; the conventional approach using drawn fused-silica capillary columns.

In conventional miniaturized technology the instrumentation has not been reduced in size; rather, it is the separation compartment size that has been significantly reduced. As an example, micro-column liquid chromatography ($\mu$LC) has been described wherein columns with diameters of 100–200 $\mu$m are employed. Another approach towards miniaturization has been the use of capillary electrophoresis (CE) which entails a separation technique carried out in capillaries 25–100 $\mu$m in diameter. Both of the above described "conventional" miniaturization technologies ($\mu$LC and CE) represent a first significant step toward reducing the size of the chemical portion of a liquid phase analytical system.

One major drawback in the current approach to miniaturization involves the chemical activity and chemical instability of silicon dioxide ($SiO_2$) substrates, such as silica, quartz or glass, which are commonly used in both CE and $\mu$LC systems. More particularly, silicon dioxide substrates are characterized as high energy surfaces and strongly adsorb many compounds, most notably bases. The use of silicon dioxide materials in separation systems is further restricted due to the chemical instability of those substrates, as the dissolution of $SiO_2$ materials increases in basic conditions (at pHs greater than 7.0).

To avoid the problems arising from the inherent chemical activity of silicon dioxide materials, prior separation systems have attempted chemical modifications to the inner silica surface of capillary walls. In general, such post-formation modifications are difficult as they require the provision of an interfacial layer to bond a desired surface treatment to the capillary surface, using, for example, silylating agents to create Si—O—Si—C bonds. Although such modifications may decrease the irreversible adsorption of solute molecules by the capillary surfaces, these systems still suffer from the chemical instability of Si—O—Si bonds at pHs above 7.0. Accordingly, chemical instability in $SiO_2$ materials remains a major problem.

However, despite the recognized shortcomings with the chemistry of $SiO_2$ substrates, those materials are still used in separation systems due to their desirable optical properties.

In this regard, potential substitute materials which exhibit superior chemical properties compared to silicon dioxide materials are generally limited in that they are also highly adsorbing in the UV region, where detection is important.

Although silicon micromachining and etching have been useful in the fabrication of miniaturized analysis systems, there are significant disadvantages to the use of this approach in creating the system. Initially, silicon micromachining is not amenable to producing a high degree of alignment between two etched or machined pieces. This has a negative impact on the symmetry and shape of a separation channel formed by micromachining, which in turn may impact separation efficiency. Secondly, sealing of micromachined or etched silicon surfaces is generally carried out using adhesives which may be prone to attack by separation conditions imposed by liquid phase analyses. Furthermore, under oxidizing conditions, a silica surface is formed on the machined or etched silicon substrate. In this regard, silicon micromachining and etching are limited by the chemistry of $SiO_2$. Accordingly, laser ablation techniques have been described in commonly owned U.S. Pat. Nos. 5,571,410 and 5,658,413 to Kaltenbach et al., the disclosures of which are incorporated by reference in their entirety, for preparing miniaturized analysis devices that address these problems.

Currently, masks for laser ablation primarily are used to define the laser illumination such that features of constant depth or through holes are ablated in the substrate to be modified. However, there are some applications that may require the various features or holes in a single substrate to have depths that are different from one another. For example, both ablated channels and through holes may be desired in a single substrate. In this case, it is not possible to perform this ablation using a single conventional mask and multiple conventional masks have been required. There are several different techniques that can be used to fabricate multiple depth parts, including the use of multiple masks, but it would be advantageous to perform the ablation of the patterns with a single mask for reasons of cost, fabrication time, alignment, and simplicity. It may be of use, however, to examine previous mask technologies used to create single depth parts. The following is a brief discussion of the fabrication and use of conventional laser masks.

Conventional Methods of Laser Mask Fabrication

Free-standing metal mask. Laser ablation masks have been fabricated using a sheet of metal through which a pattern has been cut. This mask is then used as a "stencil" such that the laser light passing through the open holes or areas through the mask ablates the pattern on the substrate. This method of mask fabrication is not always accurate since the pattern is often cut using macroscopic fabrication techniques although electrochemical or direct-write laser etching can be used to obtain greater mask pattern accuracy. Besides the resolution issue use of metal masks is also limited in that the metal mask itself is ablated in certain cases, reducing the lifetime of the mask.

Metal-on-substrate mask. The metal mask pattern can also be fabricated such that it is supported by a substrate that is UV transmissive. The substrates can be fashioned from materials such as fused silica, cultured quartz, magnesium fluoride, calcium fluoride, and lithium fluoride, all of which have fairly high resistance to damage due to the high laser fluence. The metal can be deposited on the substrate by several different means, including direct evaporation, e-beam evaporation, sputtering, and electroplating. This metal can then be patterned using lithographic means or possibly even direct-write laser ablation. This method can provide extremely accurate patterns with very small features but, again, the lifetime of this type of mask can be low due to the high energy of the laser.

Dielectric layer masks. The third type of laser mask uses a highly UV transmissive substrate onto which a series of one quarter wavelength layers of dielectric materials having alternating high and low indices of refraction are deposited (see U.S. Pat. No. 4,923,772 to Kirch et al.). This configuration with a large number of layer pairs (e.g. 30 or more) provides a highly reflective surface which can reflect over 99% of the incident laser light. This set of dielectric layers can then be patterned using lithography and wet or dry etching or, alternatively, the dielectric layers can be deposited using a liftoff technique. The result is a mask containing a highly reflective pattern of opaque areas which resist damage from the high energy laser along with areas that are highly transmissive. This method, although more complicated and expensive to fabricate than the metal-on-substrate masks, is used commonly due to its increased operational lifetime.

Holographic phase-shift masks. This type of mask can also be used to define patterns in laser light but extensive and expensive calculations are required to generate the mask pattern and fabricating the mask may also be expensive.

Overall, dielectric masks offer the best resolution and best lifetime/degradation resistance. However, due to their lower cost, metal-on-substrate masks are used in operations which do not require a high fluence laser light at the mask. These applications are most common in cases where the laser passes through image reduction optics after the pattern is defined by the mask. In this manner, the laser energy per unit area incident on the part to be ablated is X2 greater than that on the mask where X is the reduction factor. Common reduction factors are 2 to 10, resulting in energy densities at the mask 4 to 100 times less than that required to ablate the part. In certain cases where accuracy is not as much of a concern, free-standing metal masks may provide an inexpensive alternative.

There are currently several methods that can be used to ablate multiple features, each at a different depth, in a part. These methods include: (1) defining a single or possibly a few laser spot geometries (e.g. a circle a square, a rectangle) and stepping and ablating this spot over the part to define the pattern; (2) using a single mask but varying the scan speed of the laser over the patterns on the mask; (3) using multiple masks to define the features for each depth; (4) using different patterns on a single mask to define the multiple depths by moving and aligning sequential patterns on the mask to the previous ones between the ablations for each depth; and (5) using a single dielectric layer mask but have varying dielectric stack thicknesses, each stack having a different transmission coefficient, thereby allowing simultaneous ablation of features of different depths.

Direct write method. This method of ablating features with multiple depths in a single part uses a single laser spot whose shape is defined by some aperture or mask. Ablation is performed to a specific depth using this spot in a single place, then the spot position is offset slightly and the ablation is performed again. This step-and-repeat process is continued, resulting in a continuous overlapping set of ablation spots such that a constant depth hole, channel, or other feature is created. For example, a first feature with depth 1.0 is ablated using a circular laser spot and can be considered to have X number of laser pulses in each location of the circular spot. After X pulses the spot is moved $\frac{1}{6}$ the diameter of the spot (or whatever overlap is deemed appropriate) and X more pulses are performed. A second feature, with depth 2.0, can be ablated by either performing 2X pulses in each spot location or by reducing by a factor of 2 the step size between each set of ablation pulses. (Note that the process is not truly linear and the multiplication factor or step size reduction factor may in both cases not be 2.) Through holes can be created simply by increasing the number of pulses in a single location. Large through holes can be created by trepanning—creating an outline of smaller through-holes such that the center portion falls out.

The primary disadvantage to this method is that it takes a long time to ablate parts with many features. The size of the spot must be on the order of the smallest dimension of the feature currently being ablated. In certain cases this can mean ablation times of hours. A second disadvantage is that it can be difficult to get very flat bottom surfaces of the ablation patterns since the spot is moved a finite distance between each set of laser pulses.

Scan speed variation method. Using a single conventional mask, either metal-on-substrate or dielectric-on-substrate, a large laser spot can be scanned over the mask, slowing down over the areas which are to be ablated deeper. This increases the number of pulses per unit time directed at a particular point on the substrate.

The advantage to this method lies in that a conventional mask can be used to produce a pattern of multiple depths. The primary disadvantages include the difficulty in making small well-defined features (e.g. 100 microns) using the large laser spot which can be several millimeters across. In fact, all the disadvantages, besides the requirement for increased computer programming for the scan path and speed, lie in the difficulty in producing well-defined features using the large laser spot.

Multiple mask method. One method that can be used to fabricate a multi-depth feature part incorporates the use of separate laser ablation masks used sequentially, each one defining the features to be ablated to a common depth. For example, one mask can be used to define the through holes which are ablated using a specified ablation rate and ablation time (or number of pulses) while a second mask, aligned to the ablated features from the first mask, can be used to define features at the same ablation rate but at a reduced ablation time (or number of pulses). A third mask can be aligned to the previously ablated features on the part and new features with a different depth can be ablated.

One advantage to this method lies in the low cost of mask fabrication by a standard process. Other advantages include the high resolution possible for individual features and the good registration between the features defined by a single mask. The primary disadvantage lies in the difficulty of obtaining good alignment between the features on the part that were ablated using the first mask and subsequent masks. In addition, for parts where many different ablation depths are required, the cost of the masks increases linearly with the number of depths.

One-mask/multiple patterns. It is possible to fabricate a part containing ablated features with several different depths using the same basic idea as described for the multiple mask method above but only using a single mask. By fabricating a mask with several different patterns, each positioned separately from the others, each of these patterns can act as an overlay mask for a specific set of features with a common depth.

The advantage to this method is that only a single conventional mask is required and a large number of different ablation depths may be created from the single mask. The disadvantages include: the difficulty in aligning the travel of the stage holding the mask to the pattern on the mask itself; the alignment of each subsequent ablation pattern to those previous; and the pattern size restriction. The latter occurs due to the requirement of multiple patterns on the single mask. For example, if two ablation depths are required, only ½ of the mask space will be available for the first pattern (depth 1) since the second half of the mask space must be used to define the second pattern (depth 2). The second disadvantage described above is not as onerous as that for the multiple mask method since that method requires not only an x- and y-alignment but also a rotational alignment between each ablation and the one mask/multiple pattern method requires a rotational alignment only once, aligning the mask stage travel to the pattern on the mask at the beginning of the process.

One mask/varying dielectric thicknesses. The last method uses a single mask substrate onto which patterns of dielectric layer stacks of different thicknesses are deposited. Each pattern, having a certain dielectric stack thickness, has a characteristic transmission and therefore an associated ablation rate. Since these patterns on the mask define the laser ablation simultaneously, the ablation depth after a set amount of ablation time is different for each pattern.

The primary disadvantage to this method is the difficulty in making the masks with differing numbers of dielectric layer pairs on the same substrate. Laid-Open Patent Publication (Kokai) No. 07-241690.

Laser masks of different types have been used for some time with two of the earliest patents regarding such masks being U.S. Pat. Nos. 4,490,211, 4,490,210 and 4,478,677 to Chen et al. However, the reflective chromium specified for the opaque areas of the metal-on-substrate mask described in Chen et al. 1985 cannot withstand the high energy of an excimer laser for laser intensities above 100 to 200 mJ/cm$^2$.

Aluminum has also been used for the opaque areas due to its high reflectivity but the laser intensity ablation threshold for aluminum is not high enough for extended or high intensity laser illumination.

U.S. Pat. No. 4,923,772 issued in 1990 to Kirch et al. describes a multilayer dielectric reflection mask, and the methods for fabricating it, developed to allow high energy intensity laser light to be patterned. Depending on the laser wavelength and specific dielectric materials used, these masks can withstand laser intensities of up to 6000 mJ/cm$^2$.

Simultaneous ablation of multiple-depth patterns have been described in Laid-Open Patent Publication (Kokai) No. 7-241690 by Hitachi, filed Mar. 7, 1994. This patent publication teaches the use of a dielectric layer mask having patterns with different numbers of high- and low-indices of refraction dielectric layer pairs on it. The patterns with many dielectric layer pairs transmit little to no laser illumination while patterns with fewer or no dielectric layer pairs transmit some to all of the incident laser light. Although this method is quite attractive for simultaneous multidepth laser ablation, it can be difficult to fabricate the differing thicknesses of dielectric for the mask.

Laid-Open Patent Publication (Kokai) No. 7-80675 by Fujitsu, filed Sep. 17, 1993, describes a laser mask for the ablation of through holes in a polymer substrate and the simultaneous roughening or coarsening of other areas on the same substrate. The laser mask is described as having dielectric layers of different thicknesses to provide high laser intensity, no laser intensity, and weak laser intensity; the weak laser intensity is described as being just high enough to roughen the surface of the substrate. This roughening is performed to promote adhesion in subsequent processing of the substrate.

CE has become a popular separation system for both large and small solutes because, in part, such miniaturized separation techniques provide more effective system design, result in lower overhead due to decreased instrumentation sizing and, in addition, enable increased speed of analysis, decreased sample and solvent consumption and increased detection efficiency. It has been demonstrated that, particularly for macromolecule solutes, the interaction of the solute with the interior surface of the capillary column is involved in the separation process. Thus, capillary electrophoretic chromatography (CEC) can be practiced utilizing an unpacked column for this class of solutes.

CEC, as it is presently practiced, is a mode of capillary electrophoresis in which the column is packed with a particulate solid-phase packing material having a high surface area due to the size and shape of the particles. In the presence of a high electrical field, electroendosmosis occurs in the presence of the high surface area packing. The advantage of CEC is that it is a chromatographic process utilizing a plug flow profile, therefore providing separation with decreased axial dispersion. Interesting applications have been demonstrated with small molecules for CEC. However, one of the disadvantages of CEC is the difficulty in getting stable packed columns comprising 50 to 100 $\mu$m diameter capillaries packed with particles having diameters in the range of 1–2 $\mu$m.

Etching the surface of a fused silica capillary column to increase the surface area of the column has been suggested as an alternative to packing capillaries with particles. Columns prepared to have high capillary surface in this manner have been observed to increase solute separation resolution. However, as noted above, there are problems inherent in using etched silica. In addition, it is difficult to coat etched silica columns to provide a surface resistant to biofouling for use in macromolecular separations. Furthermore, such columns are subject to loss of current, indicating that they are easily damaged. Even if such etched fused silica capillary columns were not unacceptably fragile, they are limited by the intrinsic pH instability of silica and the chemical phases bonded to silica.

Accordingly, there is a need in the art for a method of producing a high-surface area substrate for preparation of CE columns and other miniaturized analysis systems. In addition, there is a need in the art for an improved miniaturized analysis system that avoid the inherent shortcomings of conventional miniaturization and silicon micromachining and etching techniques. There is also a need in the art for a single laser mask that can be used to simultaneously define the laser illumination into patterns having different energy fluences, thereby allowing the simultaneous definition in a substrate of ablated patterns having different depths. Use of conventional fabrication techniques for the fabrication of these masks allows them to be made more easily than the dielectric/dielectric mask fabrication method. The described invention is divided into three separate embodiments, all fabricated using either conventional dielectric laser mask fabrication techniques or extensions and modifications of conventional dielectric laser mask fabrication techniques.

SUMMARY OF THE INVENTION

Accordingly, is a primary object of the invention to provide a method by which a high-surface area material can be prepared.

It is yet another object of the invention to provide a polymeric substrate having high-surface area texturing prepared by the aforementioned method.

It is still another object of the invention to provide a method of preparing a miniaturized planar column having a high-surface area textured interior surface.

In one embodiment of the invention, a method of preparing a high-surface area material is provided. The method comprises using subtractive methods, such as lithographic and nonlithographic methods as described herein, additive methods, such as adsorption methods, or both subtractive and additive methods.

In one preferred embodiment, the surface of the substrate is textured using by exposing the surface to a source of laser light. Optionally, the substrate may be exposed to a source of laser light through a laser ablation mask to define a pattern of light incident on the substrate.

In another embodiment of the invention, a high-surface area textured substrate prepared by one of the aforementioned methods is provided.

In yet another embodiment of the invention, a miniaturized analysis device prepared by one of the aforementioned processes is provided.

BRIEF DESCRIPTION OF THE FIGURES

FIG. 2A and FIG. 2B are illustrative examples of an "opaque dot" grayscale mask and a "transmissive dot" grayscale mask, respectively.

FIG. 3A and FIG. 3B are illustrative example of an "opaque line and transmissive space" grayscale mask and a "transmissive line and opaque space" grayscale mask, respectively.

DETAILED DESCRIPTION OF THE INVENTION

Figure 1:
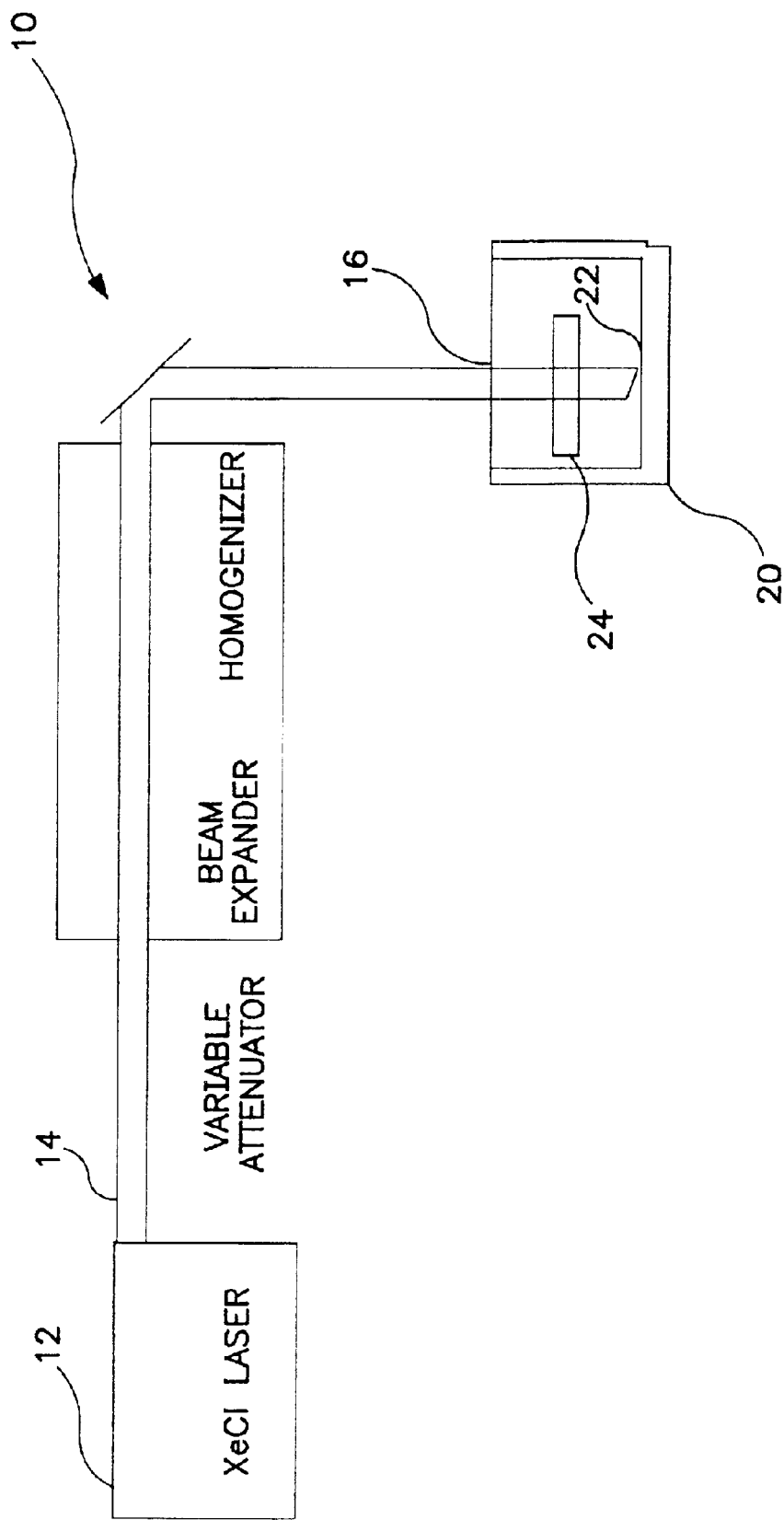
FIG. 1 is a schematic representation of a laser system by which the method of the invention may be practiced.
Figure 4A:
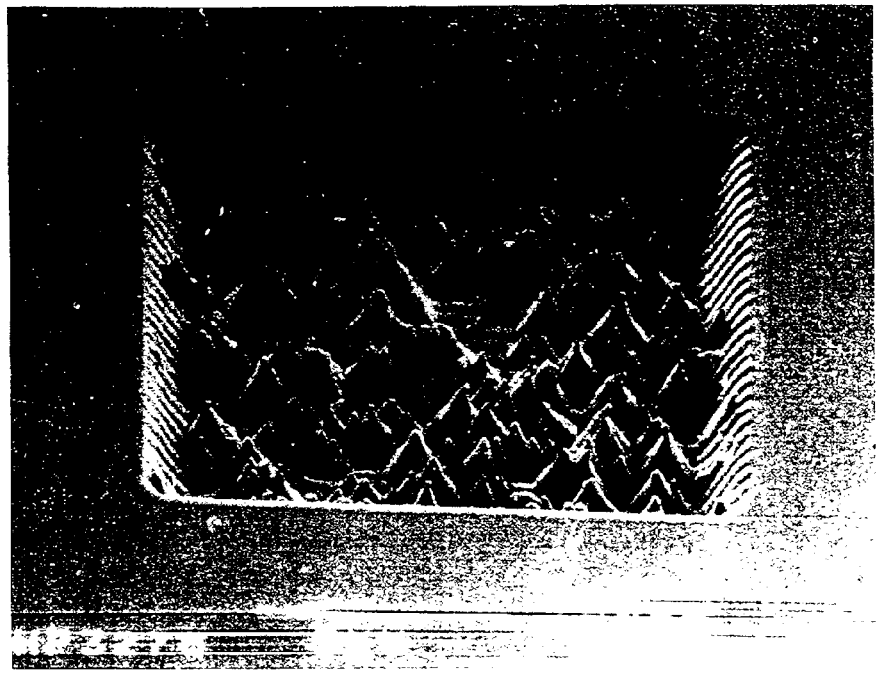
FIGS. 4A-H are scanning electron micrographs of a Kapton® sheet laser ablated through a line-and-space grayscale mask as described in Example 1.
Figure 4B:
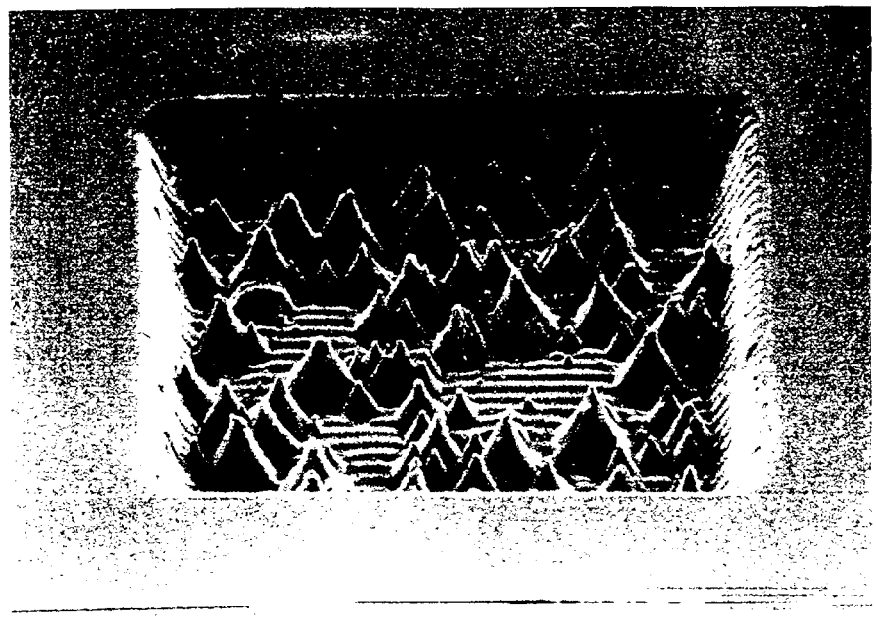
Figure 4C:
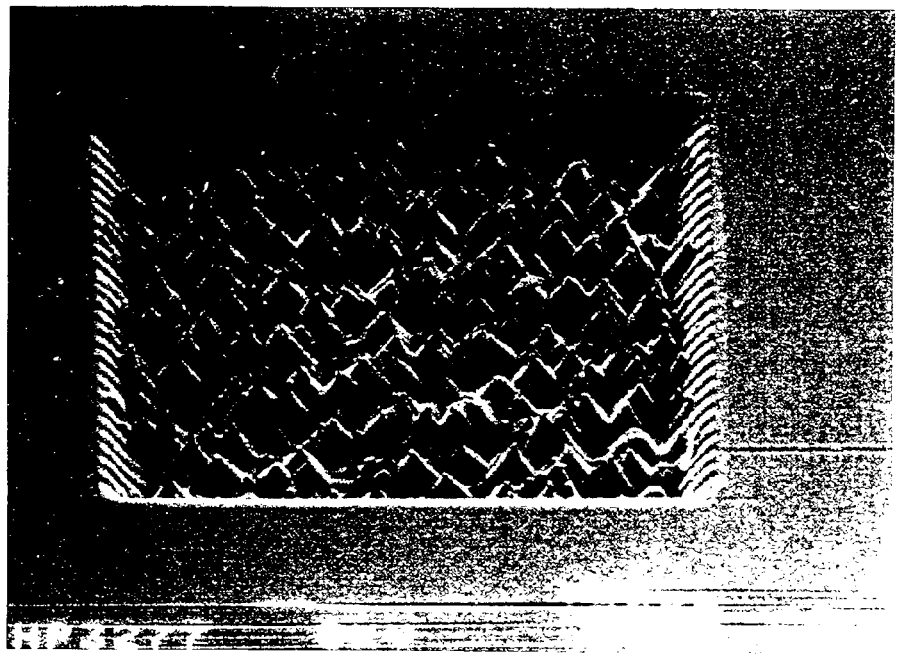
Figure 4D:
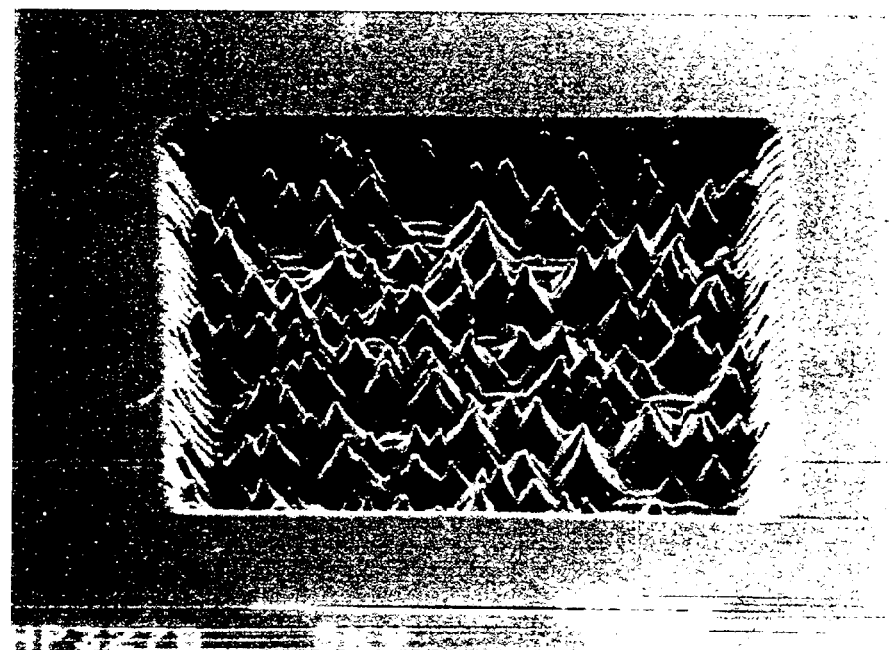
Figure 4E:
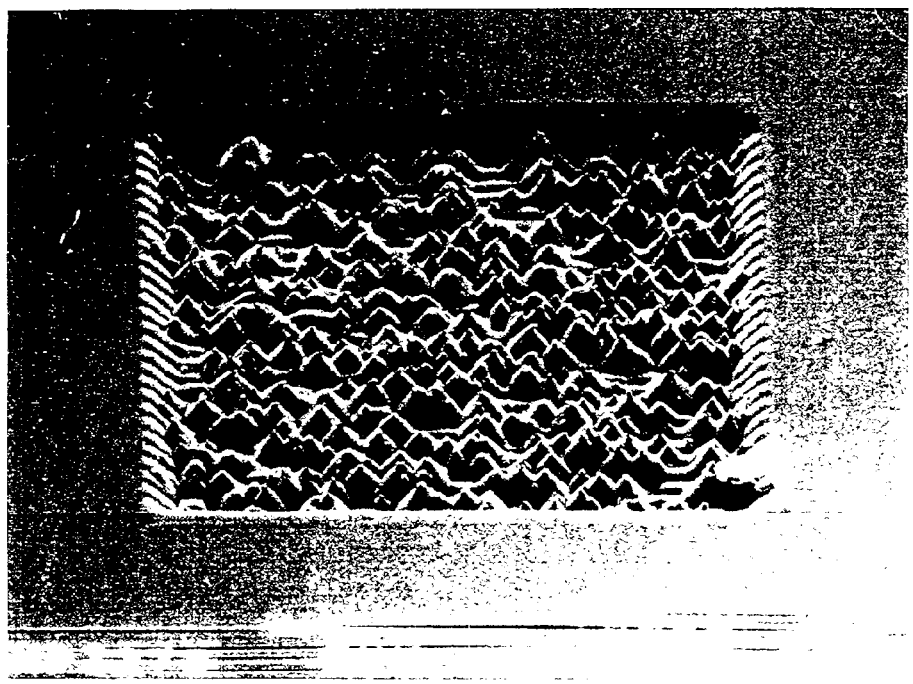
Figure 4F:
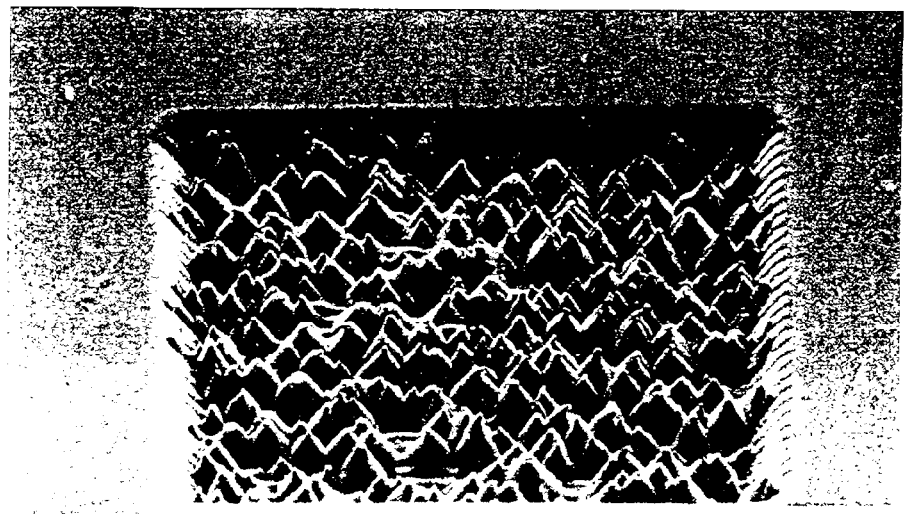
Figure 4G:
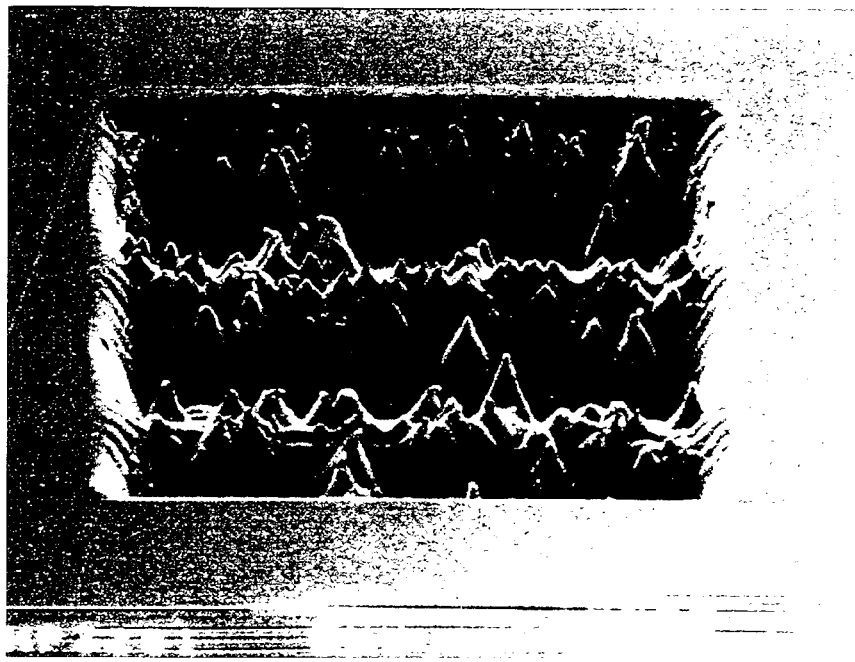
Figure 4H:
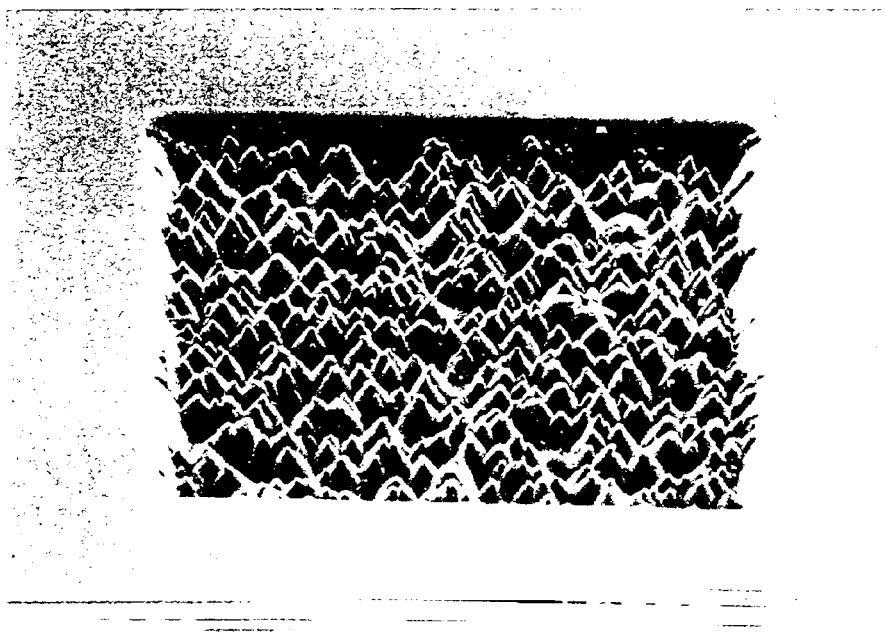

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "a mask" includes more than one such mask, and the like.

In this specification and in the claims which follow, reference will be made to a number of terms which shall be defined to have the following meanings:

The phrase "laser etching" is intended to include any surface treatment of a substrate using laser light to remove material from the surface of the substrate. Accordingly, the "laser etching" includes not only laser etching but also laser machining, laser ablation, and the like.

The term "substrate" is used herein to refer to any material that may be prepared according to the methods disclosed and claimed herein to have high surface area texturing. The substrate can be a polymer, a ceramic, a glass, a metal, a composite thereof, a laminate thereof, or the like. Preferably, the substrate is capable of being microfabricated in such a manner as to form features in, on and/or through the surface of the substrate. High-surface area materials are prepared using suitable substrates, such as laser-ablatable polymers (including polyimides and the like) and ceramics (including aluminum oxides and the like). Further, high-surface area materials are prepared using composite substrates such as laminates. A "laminate" refers to a composite material formed from several different bonded layers of same or different materials. One particularly preferred composite substrate comprises a polyimide laminate formed from a first layer of polyimide, such as Kapton® (DuPont; Wilmington, Del.), that has been co-extruded with a second, thin layer of a thermal adhesive form of polyimide known as KJ® (DuPont). This thermoplastic adhesive can be applied to one or both sides of the first polyimide layer, thereby providing a means for producing a laminate of desired thickness.

By "high-surface area" is intended a surface area that, after treatment according to the method disclosed herein, is at least 10-fold to 100,000-fold greater, preferably 1,000-fold to 100,000-fold greater, and more preferably 10,000-fold to 100,000-fold greater than the surface area of a nontreated substrate.

The term "fluence" is used for its conventional meaning of the amount of power expressed in joules of incident laser light that passes through a mask and impinges on the substrate, per unit surface area of the substrate. The "lower threshold" fluence is the level of power per unit surface area of the substrate below which laser ablation does not occur. The "upper threshold" fluence is the level of power per unit surface area of the substrate at which homogeneous ablation of the substrate occurs.

The phrase "partial transmission" or "partially transmissive" when used in reference to a mask or to a component of a mask intends that the mask or component passes less than 100% but more than 0% of incident light. The phrase "percent partial transmission" is used to refer to the average overall transmission through a particular area of a laser ablation mask. Thus, a dielectric stack that allows the passage of less than 100% of incident light is partially transmissive. A "dot" grayscale mask or a "line-and-space" grayscale mask, as described more fully below, will have areas that pass essentially 100% of the incident light and light-opaque elements that block the passage of essentially 100% of the incident light, thereby allowing passage of light which, averaged over the entire area of the mask or mask element, is less than 100% of incident light, i.e., is partially transmissive. A mask may, alternatively or in addition to light-opaque elements, comprise partially transmissive mask elements, e.g., dieletric stack elements. The percent partial transmission of a mask can be adjusted by increasing or decreasing the percent of a local area of the mask occupied by light opaque elements.

The term "resolved" or "resolution" refers to the formation of features in the substrate that resemble the features on a laser ablation mask. For example, if a laser ablation mask is used that is partially transmissive as a result of the placement thereon of laser-light opaque squares, resolution of the mask, or of features on the mask, on the substrate would result in the appearance recognizable square-shaped areas of non-ablated substrate material.

The term "surface treatment" is used to refer to preparation or modification of the surface of a substrate that will be in contact with a sample during sample treatment steps and/or analytical separation, whereby the separation characteristics of the device are altered or otherwise enhanced. Accordingly, "surface treatment" as used herein includes: physical surface adsorptions; covalent bonding of selected moieties to functional groups on the surface of treated substrates (such as to amine, hydroxyl or carboxylic acid groups on condensation polymers); methods of coating surfaces, including dynamic deactivation of treated surfaces (such as by adding surfactants to media), polymer grafting to the surface of treated substrates (such as polystyrene or divinyl-benzene) and thin-film deposition of materials such as diamond or sapphire to treated substrates.

The term "laser ablation" is used to refer to a machining process using a high-energy photon laser such as an excimer laser to ablate features in a suitable substrate. The excimer laser can be, for example, of the $F_2$, ArF, KrCl, KrF, or XeCl type.

The advantages of creating analysis devices from polymeric substrates using excimer laser ablation has been documented in U.S. Pat. Nos. 5,571,410 and 5,658,413 to Kaltenbach et al. Therefore, this approach has all the advantages of using the same process for creating the device and creating the texturing in polymeric substrates with all the inherent advantages described for devices fabricated in polymers.

Use of laser ablation techniques to create high-surface area polymeric substrates affords advantages over prior etching techniques used to form high-surface area silica substrates. Initially, the capability of applying rigid computerized control over laser ablation process allows precise control over the texturing process. The laser ablation process also avoid problems encountered with microlithographic isotropic etching, which may undercut masking during etching, giving rise to undesirable and asymmetrical surface structures.

Laser ablation further enables the creation of microstructures with greatly reduced component size. In this regard, microstructures formed according to the invention are capable of having high aspect ratios with enhanced sample processing compared with those fabricated using prior etching techniques. The use of laser-ablation processes to form microstructures in substrates such as polymers increases ease of fabrication and lowers per-unit manufacturing costs in the subject devices as compared to prior approaches such as micromachining devices in silicon. In this regard, devices formed according to the invention in low-cost polymer substrates have the added feature of being capable of use as substantially disposable miniaturized column units.

In general, any UV-absorbing substrate is a suitable substrate for laser ablation. A preferred substrate comprises a polyimide material such as those available under the trademarks Kapton® or Upilex® from DuPont (Wilmington, Del.), although the particular substrate selected may comprise any other suitable polymer or ceramic substrate. Polymer materials particularly contemplated herein include materials selected from the following classes: polyimide, polycarbonate, polyester, polyamide, polyether, polyolefin, or mixtures thereof.

Accordingly, a high-surface area polymeric substrate can be prepared by at least two general types of methods. The first type is "subtractive,", i.e., methods in which material from a preexisting surface is removed to form a high surface area finish. The second type of method is "additive," in other words methods in which material is added, e.g., adsorbed to, adhered to, bonded to, precipitated onto, or combinations thereof, a pre-existing surface to form a high surface area finish.

Method for fabricating high-surface area textured substrates, by direct feature definition, "intrinsic" feature definition, additive feature definition, and the like, include: (1) laser ablation, by direct feature definition or intrinsic feature definition, or a combination thereof; (2) lithographic methods, by masking methods, e.g., dry- and wet-etching, direct feature, e.g., LIGA and lithographic definition of photosensitive or photoreactive substrates; (3) nonlithographic methods; (4) laser-assisted chemical etching; and (5) combinations of any of the above methods. In addition, a high-surface area textured substrate can be prepared using a combination of any of the methods disclosed herein.

A direct feature definition method for creating high surface areas specifically defines the shape of the high surface area features such as tall circular, square, rectangular, or other cross-section posts, walls, or other "tall" configurations. In this method, not only is the shape of each feature predefined but also each features placement. Nominally, each feature has vertical sidewalls but this is not required or even necessarily desired. In practice, the sidewalls almost always have some non-vertical slope.

An intrinsic feature definition method for creating high surface area substrates relies on the interaction between the fabrication method and the intrinsic properties of the substrate material. For example, some chemical etches cause a roughening of a substrate surface, thereby increasing the surface area. In this type of process, the average feature definition—size, shape, and placement—can be predicted but the actual final features almost always are, to a greater or lesser extent, randomly placed and sized.

An additive feature definition method for creating high surface area substrates adds features to a substrate to create increased surface area. Examples of this process might include: bonding a plurality of high surface area particles to the substrate; lithographically defining high surface area features in an added layer of material (e.g. photoresist or photo-imagible material) whether by UV light illumination for photoresist, laser ablation, or some other method; growing through some chemical or adsorbtive process a layer or group of high surface area particles on the substrate.

There are several different types of subtractive techniques and these will be discussed in two categories: lithographic subtractive techniques and nonlithographic subtractive techniques.

Lithographic methods are those in which a pattern is generated by optical means, most commonly, but not necessarily, by using a mask with a pre-existing pattern on it. Light passes through the mask in selected areas resulting in a light pattern on a substrate. The differences in the following lithographic methods lie in the differences in how this light pattern is used.

Direct feature definition methods are those in which the substrate or one of its layers is patterned directly and then itself used as the high surface area finish. A mask is used such that a photosensitive or photoreactive substrate (or layer on a substrate) has a mask-defined light pattern incident upon it. This causes the substrate to be directly patterned based on the pattern on the mask. Alternatively, the substrate so exposed may require an additional development step to reveal the pattern thereon. The high surface area is thereby created by removal of selected material of the substrate. By choosing an appropriate pattern, a high surface area finish can be directly patterned onto a substrate. The actual shape of each local feature that makes the surface a high surface area one can be controlled. The substrate on which the high surface area finish has been created can then be used directly in the device for which it is intended or, optionally, may be used as a mold to prepare duplicates of the substrate, as described in greater detail below. Examples of this method include LIGA and LIGA-like methods, patterning substrates of
photoresist and photoresist-like materials, and laser etching.

Dry- and wet-etching are secondary masking techniques that can be used to pattern substrates. In these methods, an optical mask is used to pattern a surface layer on the top of the substrate. The patterned surface layer is then used as a mask for subsequent substrate etching procedures. This etching process can either be wet processes in
which the substrate is etched in a liquid or etched in a plasma. Examples of these methods include bulk silicon etching and deep silicon etching. It is intended that such secondary masking techniques include processes that use masks and/or masking layers on the substrate to create high surface area patterned areas in which the high surface area is created not by a specific pattern of dots, lines, or the like, but by random or probabilistic interactions. For example, reactive ion etching creates a high surface area in a specifically defined pattern on the substrate, e.g., a high surface area chamber or channel on an otherwise smooth surface. Dry- or wet-etching can be performed on a selected area or areas such that a high surface area topography is created with a random or pseudo-random distribution of size, placement, orientation and/or surface area.

In a method referred to as "deposit and pattern," a high surface area layer can be added to a previously existing substrate depositing a layer of material onto the substrate and then patterning the layer using direct lithographic feature definition or using dry- or wet-etching to produce a high surface area finish.

Non-lithographic techniques include, for example, laser-assisted chemical etching and local "roughening" of desired surfaces. In laser-assisted chemical etching, a rough surface finish can be prepared by illuminating specific areas of a substrate or layer on a substrate with a laser in the presence of some reacting gas or liquid. The input energy of the laser causes a chemical reaction to occur at the illuminated surface but not in the areas that have not been illuminated. This method would rely on a statistical probability of rough feature formation as the etch progresses.

Local "roughening" of desired surfaces can be done by laser ablation, chemical roughening after assembly, or the like. Briefly, laser ablation involves the use of an excimer laser, or other types of lasers (e.g., YAG laser), to effect an etching process that does not depend on patterning the rough "dots" individually on a substrate through a mask. Rather, this technique, described in greater detail herein, relies on a statistical probability of rough feature formation as the etch progresses.

Chemical "roughening" after assembly is a method used to form high surface area finished in, e.g., silica columns. The method is one in which a device, e.g., a column, chamber, other fluidic feature or the like, is fabricated and then a chemical or mixture of chemicals, liquid or gas, are introduced onto the surface. The chemicals etch or roughen the surface providing a high surface area finish. This method also does not explicitly define the roughening pattern (the pattern of dots or micro-features).

Non-patterned high surface area finishes can also be obtained using additive techniques, i.e., by adding material to a surface. There are several examples of additive techniques.

In one example of an additive technique, a material is selectively adsorbed, adhered, or otherwise bonded to only the desired surfaces of the substrate. Optionally, this method may be used to form surface features of a device after assembly thereof.

Deposit and pattern "molding," followed by filling with high surface area material may be used to prepare certain separation devices. For example, planar and some nonplanar devices can be fabricated and then filled with a high surface area material, much like current LC devices are made today.

Another alternative method for producing a rough surface uses a process which results in either a reaction with the surface material producing a rough surface or results in a high surface area precipitate on the surface, i.e., reactively forms a "rough" surface.

Methods for creating high surface area features using laser ablation include direct feature definition and intrinsic feature definition. Direct feature definition and intrinsic feature definition can be performed by using step-and-repeat methods using a predefined laser spot and/or by using a scanning method with a laser mask that defines the features directly, i.e., cylinders or square, rectangular, diamond-shape cross-section "towers" or the like.

The scanning method will always use a mask for direct feature definition. The mask defines the horizontal cross-section and placement of the features while the depth of the ablation controls both the aspect ratios of the features and the overall increase in surface area.

Intrinsic feature definition depends on specific properties of the material being ablated. For example, intrinsic feature definition (i.e., "roughening") using laser ablation relies on the phenomenon known as coning or cone formation. This cone formation occurs when the fluence of a laser pulse at the substrate is not high enough to completely remove a whole layer of material. Even a small particle of material that remains of the previous layer may be enough to initiate the formation of a cone or cone-like feature since this particle of material may not be removed by subsequent laser pulses but instead act as a sort of mask, creating a cone behind it as the laser ablates further down into the material around the particle. See Krajnovich et al. (1993) *J. Appl. Phys.* 73:3001–3008.

Methods for forming miniaturized planar column devices are disclosed in commonly owned U.S. Pat. No. 5,658,413 to Kaltenbach et al., supra. Briefly, the selected substrate material is laser-ablated in a pattern defined by one or more lithographic masks using laser radiation. In a preferred embodiment, such masks define all of the ablated features for an extended area of the material, for example encompassing multiple apertures (including inlet and outlet ports), micro-alignment means and separation chambers.

Alternatively, patterns such as the aperture pattern, the separation channel pattern, etc., may be placed side by side on a common mask substrate which is substantially larger than the laser beam. Such patterns may then be moved sequentially into the beam. In other contemplated production methods, one or more masks may be used to form apertures through the substrate, and another mask and laser energy level (and/or number of laser pulses) may be used to define separation channels which are only formed through a portion of the thickness of the substrate. The masking material used in such masks will preferably be highly reflecting at the laser wavelength, consisting of, for example, a multilayer dielectric material or a metal such as aluminum.

Laser ablation may be used to form miniaturized separation channels and apertures in a wide variety of geometries. Any geometry which does not include undercutting may be provided using ablation techniques, such as modulation of laser light intensity across the substrate, stepping the beam across the surface or stepping the fluence and number of pulses applied to each location to control corresponding depth.

The laser-ablated features in the miniaturized planar analysis device may be further exposed to laser-light through a laser ablation mask as disclosed herein to prepare features having high-surface area texturing.

As a final optional step in laser ablation process, a cleaning step is performed wherein the laser-ablated portion of the substrate is positioned under a cleaning station. At the cleaning station, debris from the laser ablation are removed according to standard industry practice.

In one preferred embodiment, a high-surface area polymeric substrate can be prepared by transmitting laser light of sufficient intensity or fluence and of a wavelength appropriate for the substrate and for the features to be ablated, through a lithographic mask onto the surface of the substrate, such as a polymer or ceramic material; high-surface area laser ablation will be effected in areas that are unprotected by the lithographic mask.

In laser ablation, short pulses of intense ultraviolet light are absorbed in a thin surface layer of material within about 1 $\mu$m or less to as much as 25–50 $\mu$m of the surface. Preferred pulse energies are greater than about 100 millijoules per square centimeter and pulse durations are shorter than about 1 microsecond. Greater depths of ablation can be achieved by changing the speed at which the laser light source passes over the substrate, by increasing the fluence, by increasing the number of pulses of laser light per second, by making successive passes of the laser light over the substrate, or the like.

Under these conditions, the intense ultraviolet light photodissociates the polymer material. Furthermore, the absorbed ultraviolet energy is concentrated in such a small volume of material that it rapidly heats the dissociated fragments and ejects them away from the surface of the material. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micrometer.

Although laser ablation has been described herein using an excimer laser, it is to be understood that other ultraviolet light sources with substantially the same optical wavelength and energy density may be used to accomplish the ablation process. Preferably, the wavelength of such an ultraviolet light source will lie in the 150 nm to 400 nm range to allow high absorption in the substrate to be ablated. Furthermore, the energy density should be greater than about 100 millijoules per square centimeter with a pulse length shorter than about 1 microsecond to achieve rapid ejection of ablated material with essentially no heating of the surrounding remaining material. Laser ablation techniques, such as those described above, have been described in the art. Znotins, T. A., et al., *Laser Focus Electro Optics*, (1987) pp. 54–70; U.S. Pat. Nos. 5,291,226 and 5,305,015 to Schantz et al.

Accordingly, in one embodiment the invention concerns the use of laser ablation to form high-surface area texturing of polymeric surfaces. The invention, together with additional features and advantages thereof, may be best understood by reference to the following description taken in connection with the illustrative drawings.

The laser ablation system employed in the invention generally includes beam delivery optics, alignment optics, a high precision variable speed mask shuttle system, and a processing chamber including mechanism for handling and positioning the material. In a preferred embodiment, the laser system uses a projection mask configuration wherein a precision lens interposed between the mask and the substrate projects the excimer laser light onto the substrate in the image of the pattern defined on the mask.

With reference to FIG. 1, an example of a system 10 by which a substrate may be laser ablated to form high-surface area texturing is illustrated. Generally, the laser ablation system includes beam delivery optics, alignment optics, a high precision variable speed mask shuttle system, and a processing chamber including mechanism for handling and positioning the substrate. In a preferred embodiment, the laser system uses a projection mask configuration wherein a precision lens interposed between the mask and the substrate projects the excimer laser light onto the substrate in the image of the pattern defined on the mask. In particular, as shown in the example illustrated in FIG. 1, light 14 from excimer laser 12 is passed through mask 16 and thereafter onto the surface 22 of substrate 20. Optionally, transfer lens 24 may be interposed between mask 16 and surface 22 of substrate 20. Mask 16 and substrate 20 may be placed on independently controlled X-Y translation stages or on the same X-Y translation stage. In addition, excimer laser 12 may be mounted to a moveable support means. Alternatively, a mirror or system of mirrors can be used to direct the light over the mask and/or the substrate. Using this system, light 14 from laser 12 may passed over surface 22 of substrate 20 at a predetermined rate and in any predetermined pattern.

The mask may be made of any laser-light transmissive material comprising laser-light opaque material applied thereto, a laser-light transmissive material comprising laser-light partially transmissive material applied thereto, a laser-light transmissive material comprising laser-light opaque material embedded therein, a laser-light transmissive material comprising laser-light partially transparent material embedded therein, or a laser-light transmissive material comprising a combination of laser-light opaque material applied thereto, laser-light partially transmissive material applied thereto, laser-light opaque material embedded therein, and laser-light partially transparent material embedded therein. The laser-opaque material used in such masks will preferably be highly reflecting at the laser wavelength, consisting of, for example, a multilayer dielectric material or a metal such as aluminum. The mask may be one of many different configurations. In one preferred embodiment, the mask is a "grayscale" mask which is used to selectively attenuate the laser fluence on certain areas of the substrate to be ablated. Since the laser ablation rate, i.e., the rate of substrate material removal, is dependent on the laser fluence, controlling and attenuating the laser fluence results in different rates of laser ablation of the substrate. Features having different ablation depths can be simultaneously ablated using a single mask having various transmission characteristics over the surface of the mask. In an alternative embodiment, high-surface area texturing of a substrate may be effected by using low fluence laser illumination in a scanning or step-and-repeat protocol.

A first preferred type of mask is a full transmission opaque/clear type mask with grayscale patterns, e.g., a "dot" grayscale mask, examples of which are provided in FIG. 2A and FIG. 2B. This type of mask uses laser-light opaque dots spaced a predetermined or random pitch apart on a full transmission surface or laser-light transmissive dots on an opaque background. The dots are elements of a "grayscale" area on the mask, i.e., an area over which surface the transmission averages less than 100%. The dots may be of any geometry, e.g., circles, ovals, triangles, squares, rectangles, pentagons, hexagons, or other multisided structure, and the like. A second preferred type of partially transmissive mask is a "line-and-space" grayscale mask, examples of which are provided in FIG. 3A and FIG. 3B. This type of grayscale mask uses alternating lines that are laser-light opaque on a transmissive background or laser-light transmissive on an opaque background.

In one preferred embodiment of a grayscale mask, the size of the dots and lines are selected so that the features are not resolved on the ablated surface of the substrate, i.e., so that dots or lines do not become visible on the surface of the substrate. In alternative embodiment, the size of the dots and lines are selected so that the high surface area features are optimized.

The layout of the dots, and thus the density of laser-light transmission, is expressed in terms of the size of the dot on a unit grid area. Thus, as illustrated in FIG. 2, a 2.0 $\mu$m×2.0 $\mu$m square laser-light opaque dot may be placed in a 3.0 $\mu$m×3.0 $\mu$m unit grid area. In a dot grayscale mask, the layout of the dots may be the same or different across the surface area of the mask. Thus, for example, square dots ranging in size from about 0.75 $\mu$m$^2$ to 3.0 $\mu$m$^2$ can be arranged on unit grids ranging in size from about 2.0 $\mu$m$^2$ to 4.0 $\mu$m$^2$. The percent transmission of laser light can range between greater than about 95% to less than about 5%, preferably in the range of about 95% to about 50%. However, as the size of the features increase relative to the wavelength of laser light used, there can be a loss of surface homogeneity and a resolution of the features, i.e., the pattern on the surface of the substrate resembles a dot. This may be a desirable surface area configuration in the case of direct feature definition or undesirable in the case of intrinsic feature definition.

For a line-and-space mask, the layout of the alternating opaque and transmissive lines is expressed in terms of the size of an transmissive line relative to a line-and-space pair. Thus, a 1.75 $\mu$m/3.0 $\mu$m mask will have 1.75 $\mu$m-wide transmissive lines with an overall dimension of the line-and-space pair of 3.0 $\mu$m. "Small" line-and-space grayscale patterns have transmissive lines having a width of between about 1.0 $\mu$m and 2.0 $\mu$m and a pitch between about 2.0 $\mu$m and 4.0 $\mu$m. "Large" line-and-space grayscale patterns have transmissive lines having a width of between about 2.0 $\mu$m and 4.0 $\mu$m and a pitch between about 4.0 $\mu$m and 8.0 $\mu$m, or greater. The mask may have a uniform pitch over the entire surface of the mask or, alternatively, the pitch may vary across the surface of the mask. Again, as the pitch of the features increase relative to the wavelength of laser light used, there can be a loss of surface homogeneity and a resolution of the features, i.e., the pattern resolves on the surface of the substrate and resembles the pattern on the mask. This may be a desirable surface area configuration in the case of direct feature definition or undesirable in the case of intrinsic feature definition.

Examples of laser masks include free-standing metal masks, metal-on-substrate masks, dielectric layer masks, holographic phase-shift masks, and the like.

Free-standing metal masks are laser ablation masks fabricated using a sheet of metal through which a pattern has been cut. This mask is then used as a "stencil" such that the laser light passing through the open holes or areas through the mask ablates the pattern on the substrate.

Metal-on-substrate masks are metal mask patterns that are fabricated such that it is supported by a substrate that is UV transmissive. The substrates can be fashioned from materials such as fused silica, cultured quartz, magnesium fluoride, calcium fluoride, and lithium fluoride, all of which have fairly high resistance to damage due to the high laser fluence. The metal can be deposited on the substrate by several different means, including direct evaporation, e-beam evaporation, sputtering, and electroplating. This metal can then be patterned using lithographic means or possibly even direct-write laser ablation. This method can provide extremely accurate patterns with very small features.

Dielectric layer masks use a highly UV transmissive substrate onto which a series of one quarter wavelength layers of dielectric materials having alternating high and low indices of refraction are deposited (see attached U.S. Pat. No. 4,923,772). This configuration with a large number of layer pairs (e.g., 30 or more) provides a highly reflective surface, which can reflect over 99% of the incident laser light. This set of dielectric layers can then be patterned using lithography and wet or dry etching or, alternatively, the dielectric layers can be deposited using a lift-off technique. The result is a mask containing a highly reflective pattern of opaque areas, which resist damage from the high energy laser along with areas that are highly transmissive.

Holographic phase-shift masks are described in Holmer et al. (1995) *Applied Optics* 34:7718–7723, and references cited therein.

The process by which the high-surface area texturing of the substrate is prepared involves exposing the surface of the substrate to a source of laser light, preferably, but not necessarily, through a partially transmissive mask or a holographic phase-shift mask. The process may involve scanning the surface of the substrate with the masked laser light. The extent of ablation of the substrate depends in part on the scan speed. Greater ablation of the surface of the substrate can be achieved by using slower scan speeds. For example, and in no way to provide any limitation on the scan speeds that are acceptable using the methods described herein, the speed at which the laser light is passed over the substrate is in the range of about 0.1 mm/sec to about 100 mm/sec, preferably in the range of about 10 mm/sec to 50 mm/sec, more preferably in the range of about 15 mm/sec to 35 mm/sec. Generally, this method can be applied using any scan rate as well as a step-and-repeat protocol, i.e., in which a laser spot, possibly with a defined shape, is moved incrementally from place to place over the substrate, thereby creating an ablated pattern. Alternatively, the laser spot may be kept stationary and the substrate moved with respect to the spot.

In addition, the laser ablation process may involve multiple exposures of the surface of the substrate to laser light using the same or a series of different grayscale masks. The series of laser ablation masks may be of the same or different patterns, i.e., one or more dot grayscale masks having the same or different pattern and/or one or more line-and-space grayscale masks having the same or different pitches, may be used sequentially and in any order. Optionally, the surface may be exposed to laser light through a 100% transmission mask, i.e., a mask that passes essentially all of the incident laser light, at any stage of the process.

High-surface area texturing of a substrate can also be effected by a combination of scanning the source of laser light over the surface of the substrate, exposing the surface to laser light using a step-and-repeat protocol, and subjecting the substrate to multiple exposures of laser light.

The scanning and step-and-repeat methods of preparing a high-surface area textured substrate can be used to expose the entire surface of the substrate to laser light or only selected areas of the substrate. Selected areas of the substrate may be exposed to a source of laser light using a mask by which exposure of selected areas is prevented, by selectively turning the source of laser light on or off, or by any means well known in the art to selectively limit the exposure of the substrate.

The claimed method can also be used to prepare miniaturized analysis devices using laser ablation in a suitable substrate. Analysis devices can be formed using injection molding techniques wherein the original microstructure has been formed in the substrate by any of the aforementioned methods.

More particularly, microstructures such as separation compartments are formed in a planar substrate by excimer laser ablation. A frequency multiplied YAG laser may also be used in place of the excimer laser. In such a case, a complex microstructure pattern may be formed on a suitable polymeric or ceramic substrate by combining a masking process with a laser ablation means, such as in a step-and-repeat process, where such processes would be readily understood by one of ordinary skill in the art. High-surface area texturing of the separation compartments or other features on the device is effected by interposing a laser ablation mask between the source of laser light and the substrate. Miniaturized analysis devices constructed as disclosed herein are useful in any analysis system performed on either small and/or macromolecular solutes in the liquid phase and may employ chromatographic and/or electrophoretic separation means. The device comprises microchannels and chambers for sample preparation, separation and detection. For example, a biological sample such as blood, urine, milk, cell or tissue extract, fermentation product or the like is added directly to the device. The sample is then prepared as required for the particular separation process to be performed, i.e., filtration, solid phase extraction, capillary electrophoresis or liquid chromatography. The prepared sample is then shunted to a separation chamber, and immediately following separation, detected by any of a number of means well known in the art.

In particular, a miniaturized analysis device useful for sample processing can be prepared by microfabricating a channel in the surface of a substrate which, when mated with a cover plate or a mirror image of the substrate in which a corresponding channel has been fabricated, forms, for example, a separation chamber. As noted above, such a device and a method of preparing such a device are disclosed in U.S. Pat. No. 5,658,413 to Kaltenbach et al., supra. The channel can be prepared to have a high-surface area textured surface using the methods disclosed and claimed herein. The texturing of the surface of the channel can be homogeneous, i.e., uniform throughout the channel, i.e., both across and along the linear axis of the channel. Alternatively, the texturing of the channel can be heterogenous, i.e., the texturing is not uniform across or along the linear axis of the channel or both across and along the linear axis of the channel. The heterogeneity of the texturing may be either continuous, e.g., there can be a continually changing texturing, or discontinuous, e.g., there can be segments of distinct heterogeneous texturing. In addition, the channel surface of the substrate can be prepared to have a mixture of homogeneous and heterogeneous regions or segments as the application of the device requires.

The mode of separation that can be effected using miniaturized analysis devices comprising channels having high-surface area textured features can be chromatographic separation, electrophoretic separation, and combinations of chromatographic and electrophoretic separation modes. These separation modes can be performed using channels having a surface treatment, i.e., channels that have a high-surface area surface that is prepared or modified such that the separation characteristics of the device is altered by adsorption, bonding or coated as described above, or otherwise enhanced. Examples of selective chromatographic separation modes include "normal" phase separation, reverse phase separation, hydrophobic interaction separation, ion exchange separation, affinity capture separation, and combinations of these modes. Thus, for example, reverse phase separation may be effected in a separation compartment formed from a channel to which has been bonded, on which has been adsorbed or which has been coated with a $C_{18}$ moiety. Similarly, ion exchange separation may be effected in a separation compartment formed from a channel to which has been bonded, on which has been adsorbed or which has been coated with a member of a series of strong or weak anion or cation exchanger, or a combination of strong and weak anion or cation exchangers. Examples of electrophoretic separation modes include preparing a separation compartment from a channel that presents to the sample a physically tortuous path, filling the interstitial spaces of a channel having a high-surface area texture with a gel, e.g., a cross-linked or uncrosslinked polymeric composition such as polyacrylamide which may or may not be bonded to the surface of the channel, packing the interstitial spaces of a channel having a high-surface area texture with a material, e.g., particles, that provide selective separation characteristics.

In another embodiment, the miniaturized analysis device can be prepared to provide "n-dimensional" separation modes. For example, a two-dimensional device can be prepared in which a channel having a high-surface area texture serves as the first-dimension separation mode. A second-dimension, preferably orthogonal to the first, can be microfabricated on the surface of the device to have a high-surface area texture and configured such that the sample separated in the first dimension can be further processed by separation in the second dimension. The first and second dimension separation modes can be the same or different and can be any of the above described modes. In addition, the surfaces of the first and second dimension features of the substrate can be used as a high-surface area textured separation mode or may be prepared or modified to have a surface treatment or packing as described above. The surface treatments of the first and second dimension features can be the same or different.

The high-surface area textured substrate disclosed and claimed herein can be used as a master for preparing duplicate structures containing the high-surface area features. Thus, for example, the substrate may be used as a master mold from which a duplicate may be made. Alternatively, the substrate may be used as a stamp or as any other means well known in the art by which a duplicate may be made.

The disclosed method of fabricating a laser ablation mask is divided into four separate Types, 1–4, all fabricated using either conventional dielectric laser mask fabrication techniques or extensions and modifications of conventional dielectric laser mask fabrication techniques. These Types and/or their fabrication methods can be combined to form other types of masks.

Fabrication Using Metal Layer Patterning:

Method A: After deposition, the metal layer is patterned or selectively removed such that a pattern of the metal remains on the surface of the dielectric stack. The metal can be removed in several ways, including laser ablation and, most commonly, selectively protecting (masking) the areas where the metal is to remain with photoresist and then using a wet or dry etch to remove the exposed metal.

Method B: Alternatively, the metal can be deposited in a pattern using a lift-off process in which a patterned sacrificial layer (e.g. photoresist or other material) is deposited directly on the dielectric stack and the metal is then deposited using tan evaporation process, an e-beam evaporation process, or sputtering. The deposited metal adheres to the dielectric stack but the metal deposited on the sacrificial layer is "lifted off" when the sacrificial layer is removed.

Fabrication Using Dielectric Stack Patterning:

There are at least four basic methods of patterning a dielectric stack: (1) the stack can be dry-etched using photoresist as a defining mask; (2) the stack can be wet etched using the photoresist or metal as a defining mask; (3) the stack can be dry-etched using the metal as a defining mask; and (4) the stack can be defined during deposition using the lift-off process described above for the metal by sputtering dielectric materials instead of metal. Methods (1), (2), and (4) separate the metal and dielectric stack patterning processes completely. Method (3) requires that first the metal layer pattern be defined and used as the mask to protect the areas defining the desired pattern for the dielectric stack. Then the dielectric stack is etched/patterned. Method (3) is the preferred method of dielectric patterning.

EXAMPLE 1

A 308 nm excimer laser was used to laser ablate a sheet of Kapton®. The nominal fluence of the laser light at the surface of the Kapton® sheet was approximately 450±100 mJ/cm$^2$. The scan speed of the mask and the substrate relative to the light source was approximately 23 mm/sec. One pass of the laser light through the mask over the surface of the substrate resulted in laser ablation to a depth of 35±5 μm. All mask patterns were equally illuminated by the laser such that all differences in the resulting patterns are due to differences in the mask patterns themselves.

FIGS. 4A-H are scanning electron micrographs of a Kapton® sheet laser ablated through a line-and-space grayscale mask having a transmissive line width/line pitch (percent transmission) of 4.0 μm/17.0 μm (57%), 4.0 μm/6.0 μm (67%), 3.5 μm/7.0 μm (50%), 3.5 μm/6.0 μm (58%), 3.0 μm/7.0 μm (43%), 3.0 μm/6.0 μm (50%), and 2.5 μm/5 μm (50%), respectively.

One notable aspect of the SEM photographs is the presence of features referred to as "cones." Coning, i.e., the process that produces the cones, is an oft-observed phenomenon in the ablation of polymers when performing low-fluence ablation, i.e., near the ablation threshold of the substrate (see, e.g., Krajnovich et al. (1993) *J. Appl. Phys.* 73:3001–3008. Addition observations can be made from FIGS. 4A–G:

(1) the higher transmission patterns resulted in deeper ablation, while the lower transmission patterns resulted in shallower ablation;

(2) coning appears to be more prevalent in areas that have the lowest nominal transmission through the laser mask and covers a greater percentage of the ablation area with decreasing transmission;

(3) lines corresponding to the line-and-space grayscale were partially resolved (see the bottom and sides of the ablated areas); and (4) the size of the cones appears at least in part to be dependent on the transmission value with the larger transmission resulting in larger cones.

It appears that at a constant transmission percentage there is a correlation between the total number of cones in an area and the size of the transmissive lines; there is a larger total number of cones for a smaller width of transmissive lines. Since the total nominal illuminated are on the substrate is the same for any given transmission percentage, the reason for this is not clear. However, it follows that, since there is a certain "blur" at each opaque line edge in which some laser illumination impinges on the adjacent nominally dark area, and since there is a larger number of small transmissive/opaque lines required to fill a given area, there are a larger number of points within the total ablation area which have low to very low fluence that are ideal for initiating coning.

EXAMPLE 2

Type 1: Dielectric/Metal Two-Fluence Laser Mask

Figure 5:
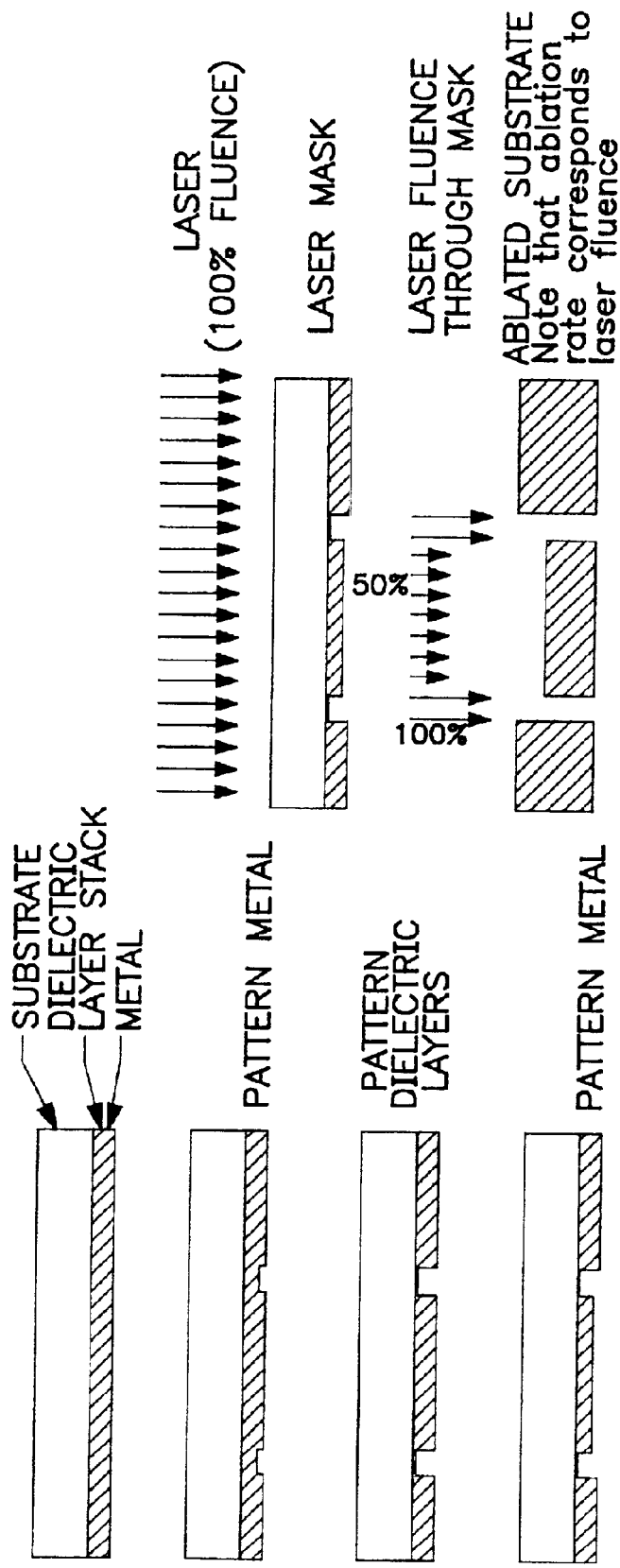
FIG. 5 provides an illustrative example of a single dielectric/metal layer two-fluence ablation mask, and a schematic illustrating a method by which such a mask can be fabricated as described in Example 2.

A dielectric/metal two-fluence laser mask and the fabrication process therefor are illustrated in FIG. 5. This type of mask is composed of a transparent substrate onto which a partially transmitting (e.g., about 50%) dielectric stack is deposited. The dielectric stack may be deposited by sputtering, followed by a deposition of a layer of metal by evaporation or sputtering. The metal layer is patterned such that the metal is removed in areas both where full transmission is desired as well as where partial transmission is desired. The dielectric stack is patterned such that it is removed only in those places where full transmission is desired. In this manner, in the areas where both the metal layer and the dielectric stack remain on the substrate there is no transmission of the laser, where only the dielectric stack remains on the substrate there is reduced transmission, and where neither the metal layer nor the dielectric stack remains there is full transmission.

EXAMPLE 3

Type 2: Combined Dielectric Mask

Figure 6:
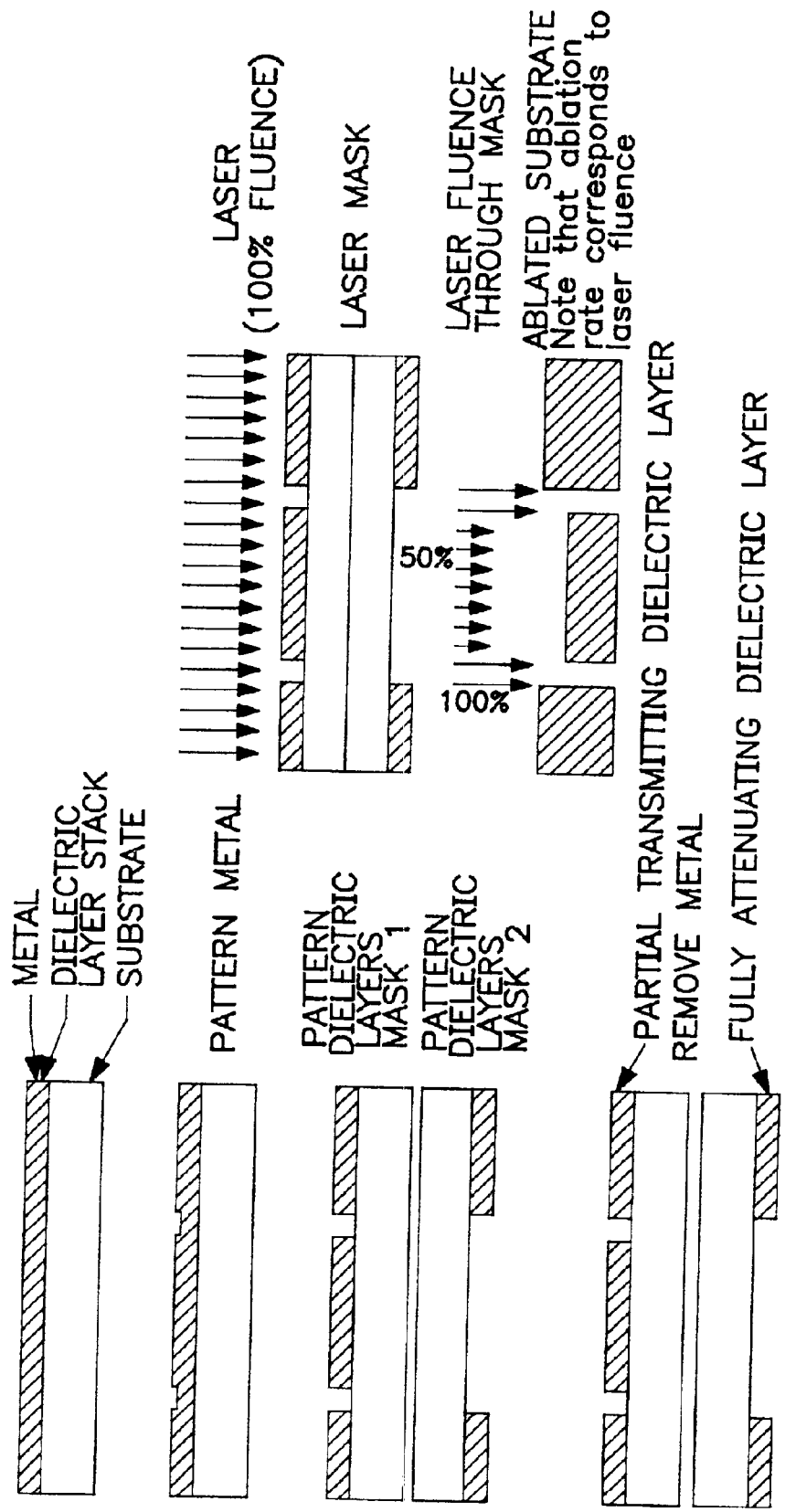
FIG. 6 provides an illustrative example of a combined/two dielectric layer two-fluence ablation mask having a back-to-back configuration, and a schematic illustrating a method by which such a mask can be fabricated as described in Examples 3 and 4.
Figure 7:
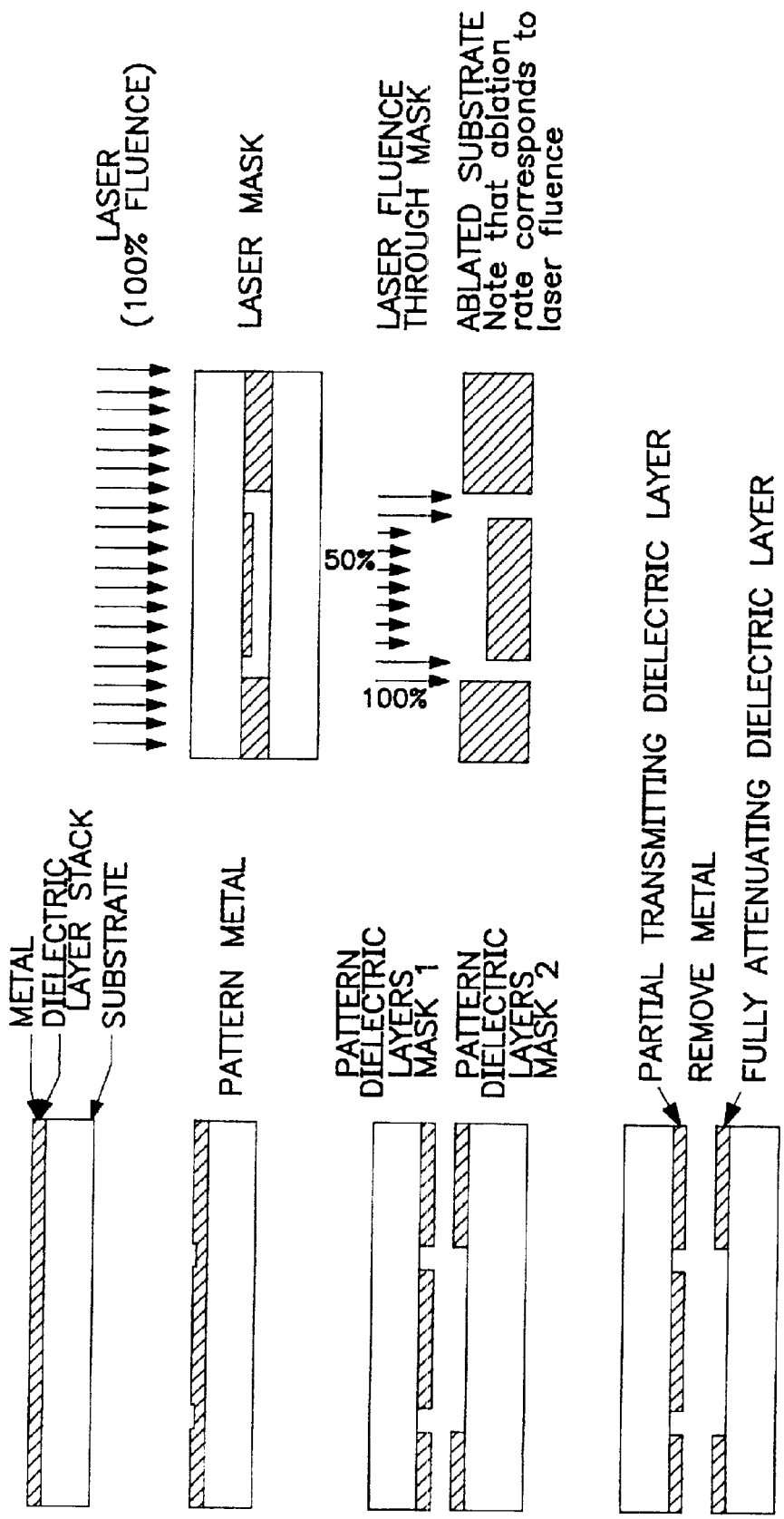
FIG. 7 provides an illustrative example of a combined/two dielectric layer two-fluence ablation mask having a front-to-front configuration, and a schematic illustrating a method by which such a mask can be fabricated as described in Examples 3 and 5.

The configuration of a combined dielectric mask and the fabrication process therefor are illustrated in FIG. 6 and FIG. 7.

A combined dielectric mask is composed of two separately fabricated dielectric masks that are combined into a single mask after fabrication. The first mask is fabricated as the Type 1 mask described in Example 2 using a partially transmissive dielectric stack such that low, partial, and full transmission can be achieved with the first mask at this stage of the fabrication process. The metal layer is then removed from the first mask. The second component of the Type 2 mask configuration is fabricated similarly to the standard dielectric stack mask for single transmission level laser patterning. The dielectric stack for the second component is fully reflecting (i.e., less than 1% transmission of the laser occurs) and this dielectric stack and the defining metal layer have the same pattern after definition as shown in FIG. 6 and FIG. 7. The metal layer is then removed from the second mask. First and second masks are then combined, or stacked together, to form a single mask. Either first or second mask can be set in front of the other with respect to the laser source.

EXAMPLE 4

Type 2A: Combined Dielectric Mask—Back-to-Back Configuration

This mask, illustrated in FIG. 6, combines first and second masks as described in Example 3, such that the surfaces of the mask substrates opposite those of the dielectric stacks are in contact and the low transmission areas of the first mask are aligned exactly with the low transmission areas of the second mask.

EXAMPLE 5

Type 2B: Combined Dielectric Mask—Front-to-Front Configuration

This mask, depicted in FIG. 7, combines first and second masks as described in Example 3, such that the surfaces of the mask substrates on which the dielectric stacks were fabricated are in contact and the low transmission areas of the first mask are aligned exactly with the low transmission areas of the second mask. First and second masks can also be combined such that the back of one mask contacts the front of the other but the front-to-back configuration gives the general sense of the method.

There are at least two advantages to a Type 2B mask over a Type 2A mask. First, the alignment of the first mask and the second mask to one another depends on aligning the dielectric features of each to one another and it is much easier to align features that are in the same focal plane as in the case of Type 2B rather than in the case of Type 2A in which the dielectric stacks are separated by the combined thicknesses of both substrates. Second, some methods of laser mask use require that the mask pattern be positioned at a specific point along the light path of a converging or diverging laser for the final illumination/ablation pattern to be in focus. The Type 2A mask has the dielectric pattern in two very separate points along the laser light path and could produce undesired effects in the final light pattern.

EXAMPLE 6

Type 3: Two-sided Dielectric Mask

Figure 8:
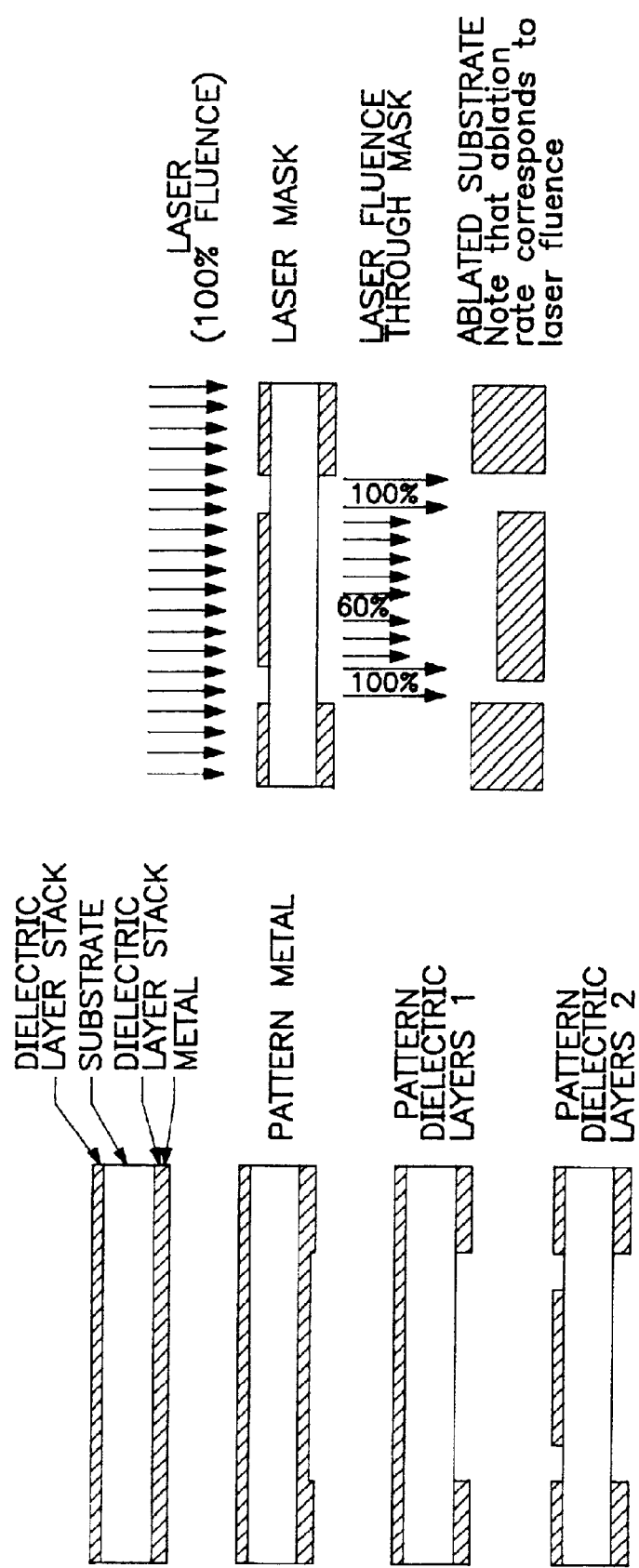
FIG. 8 provides an illustrative example of a combined dielectric metal/layer two-fluence ablation mask, and a schematic illustrating a method by which such a mask can be fabricated as described in Examples 6 and 7.
Figure 9:
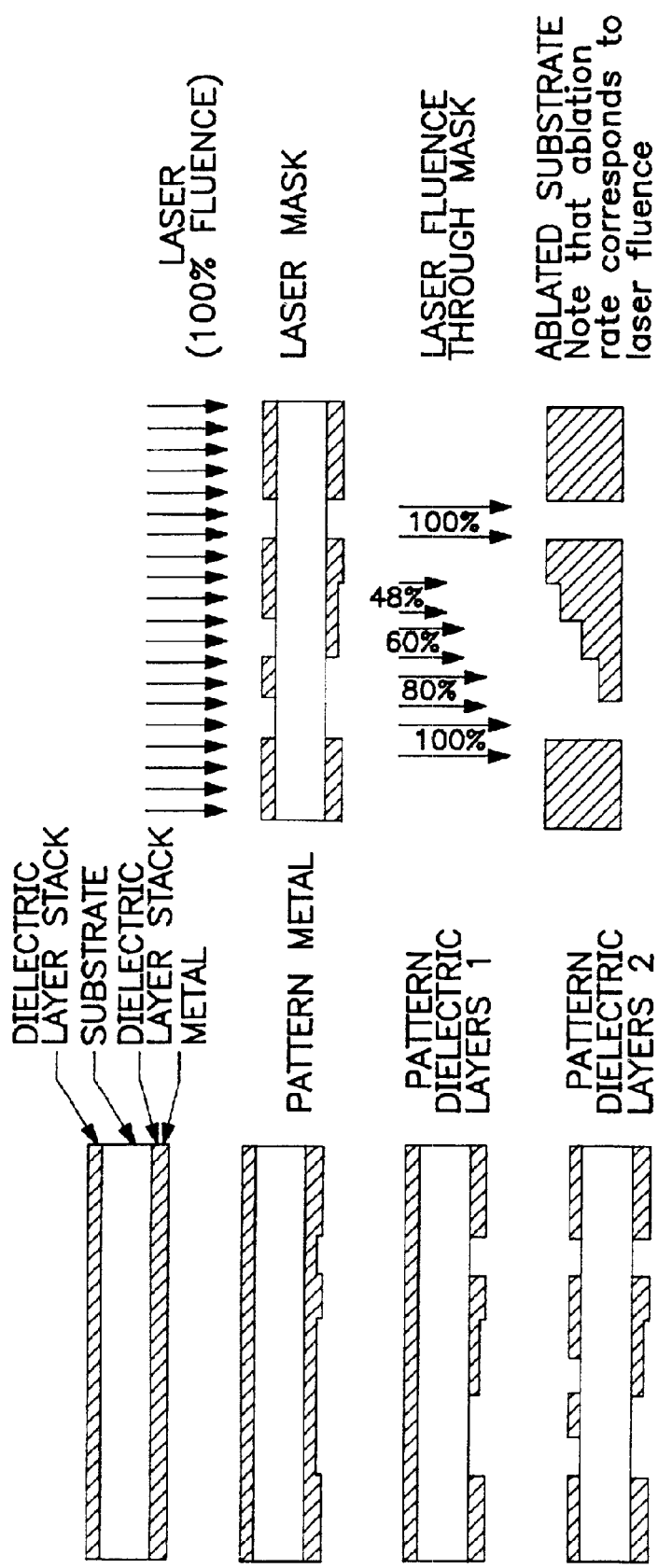
FIG. 9 provides an illustrative example of a double dielectric metal/layer multifluence ablation mask, and a schematic illustrating a method by which such a mask can be fabricated as described in Examples 6 and 8.
Figure 10:
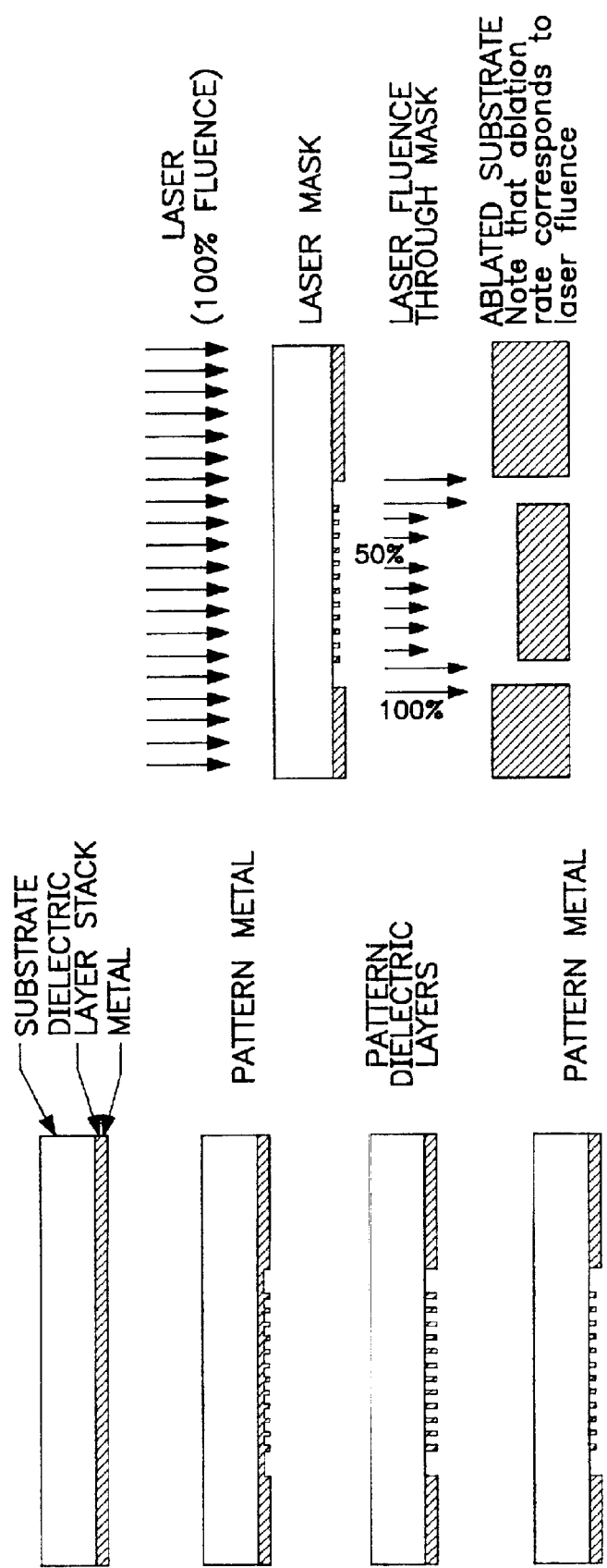
FIG. 10 provides an illustrative example of a single dielectric metal/layer grayscale ablation mask, and a schematic illustrating a method by which such a mask can be fabricated as described in Example 9.

An example of the configuration of a Type 3 mask and fabrication processes thereof are illustrated in FIG. 8 and FIG. 9.

The two-sided dielectric mask is similar the Type 2A mask except that instead of fabricating the two dielectric stacks on two separate transparent substrates as in the Type 2A mask, the dielectric stacks in the Type 3 mask are deposited and patterned on both the first and second opposing sides of a single substrate using exactly the same techniques used to fabricate the Type 2 A mask. The only difference lies in the need to perform front-to-back side alignment during fabrication so that the dielectric stack pattern on the front aligns to that on the back side of the substrate.

EXAMPLE 7

Type 3A: Two-sided Dielectric Mask—Two Fluence Mask

A Type 3A mask and method of preparing same are illustrated in FIG. 8.

The method of making a Type 3A mask replicates that used to make a Type 2A mask in configuration and use except the distance between the dielectric stack patterns on the substrate is only the thickness of one substrate rather than the thickness of two substrates as in the Type 2A mask.

EXAMPLE 8

Type 3B: Two-sided Dielectric Mask—Four Fluence Mask

A Type 3B mask and method of preparing same are illustrated in FIG. 9.

This mask uses a dielectric stack which transmits a predetermined percentage of the laser light, another dielectric stack which transmits a predetermined percentage on the opposing side of the substrate, and a metal layer on top of the dielectric stack of the backside of the substrate. The metal layer stops any remaining laser light after it passes through the previous dielectrics and substrate. Four different transmission percentages can be defined using this configuration. For areas where there is no dielectric stack the transmission is 100% (minus the losses due to the substrate itself). For areas covered only with the 80% dielectric stack, transmission is 80%. For areas covered only with the 60% dielectric stack, transmission is 60%. For areas covered with both the 80% and 60% dielectric stacks, the transmission is 40%. And for areas covered by both dielectric stacks and the metal layer the transmission is zero.

EXAMPLE 9

Type 4: Standard Dielectric Mask: Grayscale Patterns

This method uses a standard dielectric layer mask. The laser light transmission is modulated by the use of different size dots and/or lines and spaces. The average laser light transmission per unit area over a pattern can be modified by introducing a certain density of small opaque or reflective features such as dots or lines. For example, if 30% of a given area is covered in small opaque or reflective dots, the laser light transmission can be considered to be 70% if the dots are small enough so that they are not defined at the target surface. If the dots are too large, the dots will be patterned on the substrate.

EXAMPLE 10

Application Using Mask Prepared as as Disclosed Herein

Examples of use for simultaneous multi-depth ablation using any of the above masks are for the fabrication of fluidic devices requiring through holes and channels defined in U.S. Pat. No. 5,500,071 to Kaltenbach et al. and U.S. Pat. No. 5,5771,410 to Swedberg et al.

Thus, the invention provides a novel method of preparing a high-surface area textured polymeric substrate, substrates made using this method, as well as methods of preparing laser ablation masks and laser ablation masks prepared thereby. Although preferred embodiments of the subject invention have been described in some detail, it is understood that obvious variations can be made without departing from the spirit and the scope of the invention as defined by the appended claims.

We claim:

1. A substrate comprising:

a material selected from the group consisting of polymeric materials, ceramic materials, glass materials, metal materials, and composites thereof; and a surface having features formed by the treatment of a surface-altering process that utilizes a partially transmissive mask that allows a fraction of light to pass therethrough, the surface area of the treated surface being greater than the surface area of an untreated surface.

2. The substrate of claim 1, wherein the surface area of the treated surface is at least 1,000 times greater than the surface area of an untreated surface.

3. The substrate of claim 1, wherein the material comprises a polyimide.

4. An analysis device comprising the substrate of claim 1.

* * * * *